| United States Patent [19] | [11] Patent Number: 4,654,314 |
| --- | --- |
| Takagi et al. | [45] Date of Patent: Mar. 31, 1987 |

[54] POROUS CERAMIC MATERIAL AND PROCESSES FOR PREPARING SAME

[75] Inventors: Shigehide Takagi, Narashino; Shigeru Yamauchi, Tokyo, both of Japan

[73] Assignee: Sumitomo Cement Co., Ltd., Tokyo, Japan

[21] Appl. No.: 628,600

[22] Filed: Jul. 6, 1984

[30] Foreign Application Priority Data

Jul. 9, 1983 [JP] Japan ................... 58-124087
Jul. 9, 1983 [JP] Japan ................... 58-124085

[51] Int. Cl.$^4$ ............................................. C04B 38/06
[52] U.S. Cl. ........................................ 501/82; 501/80; 501/83; 501/85; 501/1; 264/44; 623/16
[58] Field of Search ............... 501/80, 82, 83, 85, 501/1; 264/44; 128/92 C; 3/1.9

[56] References Cited

U.S. PATENT DOCUMENTS

| | | | |
| --- | --- | --- | --- |
| 1,934,383 | 11/1933 | Stafford | 501/85 |
| 1,992,916 | 2/1935 | Johnson | 501/83 |
| 3,416,935 | 12/1968 | Einstein et al. | 501/82 |
| 3,497,455 | 2/1970 | Ahr | 501/83 |
| 3,929,971 | 12/1975 | Roy | 128/92 C |
| 4,371,484 | 2/1983 | Inukai et al. | 501/1 |
| 4,503,157 | 3/1982 | Hatahira | 3/1.9 |

FOREIGN PATENT DOCUMENTS 58-58041 4/1983 Japan ........................................ 3/1.9

*Primary Examiner*—William R. Dixon, Jr.
*Assistant Examiner*—Steven Capella
*Attorney, Agent, or Firm*—Sherman and Shalloway

[57] ABSTRACT

A porous ceramic material composed of a sintered porous body of a calcium phosphate compound is described. A multiplicity of capillary void paths having a diameter of 1 to 30 μm and a multiplicity of pores having a diameter of 1 to 600 μm are formed in the sintered porous body. At least part of the pores are connected to the exterior space of the sintered porous body through at least a part of the capillary voids. The porous ceramic material is valuable as a medical material, e.g., a substitute or prosthesis for bone or dental root, and also an electronic material and a genetic engineering material.

When the porous ceramic material is embedded in a bone defect of human or animals, osteolytic cells, osteoblasts, erythrocytes and body fluid are selectively allowed to intrude through the porous ceramic material while almost no intrusion of osteoclasts and collagen fibers is allowed. Accordingly, the porous ceramic material can be utilized for inducing new-born bone, controlling resorption of bone with age, remedying bone defects.

17 Claims, No Drawings

POROUS CERAMIC MATERIAL AND PROCESSES FOR PREPARING SAME

BACKGROUND OF THE INVENTION

(1) Field of the Invention

The present invention relates to a porous ceramic material and a process for the preparation thereof. More particularly, it relates to a porous ceramic material having a multiplicity of pores having a specific size and a multiplicity of capillary void paths having a specific size and connecting the pores to the exterior space of the porous ceramic material, which is valuable as a material for regeneration of bone and other medical purposes and also an electronic material or a genetic engineering material, and processes for the preparation thereof. It also relates to a method of remedying a defect of bone of a human or animal.

(2) Description of the Prior Art

A calcium phosphate compound such as hydroxyapatite or a solid solution thereof has a good compatibility with a living body and is valuable as a medical material such as an osteogenetic material, for example, a substitute or prosthesis for a bone or dental root. For example, Japanese Unexamined Patent Publication No. 56-54841 discloses a filler for a bone defect or antrum, which comprises a calcium phosphate compound powder of the apatite type crystal structure.

Furthermore, Japanese Unexamined Patent Publication No. 56-166843 discloses a filler for a bone defect or antrum, which is composed of a porous body of a calcium phosphate compound. In pores contained in this porous body of the calcium phosphate compound, the maximum pore diameter is 3.00 mm and the minimum pore diameter is 0.05 mm. These pores have such a shape and size that bone-forming components of a living body can easily intrude into these pores. This porous body has a substantially continuous three-dimensional network structure.

These conventional calcium phosphate compounds have problems in that deformation is caused with the lapse of time after a surgical treatment such as filling or prosthesis or hardening is promoted in the soft contact tissue near the filled or embedded portion, whereupon the resulting abnormal tissue must be excised. When remedying of a defect of the hard tissue of a living body caused by excision a bone tumor, bone resorption with age or external damage of a bone, it is most preferred that natural healing be promoted. Substitution or prosthesis by an artificial product is not always preferred. When such an artificial article is filled in a living body or included in a living body by prosthesis, it is most preferred that the artificial product be consumed in the living body in due course and the natural living tissue be regenerated instead to repair the defect. In this case, it is important that the speed of substitution of the artificial article by the living tissue (namely, the turnover speed) should be appropriate. If the turnover speed is excessively high, trouble such as inflammation is caused in the treated portion, resulting in complications, for example, development of cancer. In the case where the turnover speed is low and the artificial article is present in a living body for a long time, deformation of the bone tissue or other living tissues in the treated portion or hardening of the soft tissue near the treated portion is caused, whereupon excision becomes necessary in some cases.

In order to cope with the foregoing problems, it is important that a filler or prosthetic material inserted in a living body satisfy the requirements for induction and substitution of the living body tissue at a cell level. More specifically, it is important to appropriately promote the activation of an osteolytic cell (osteolysis) and an osteoblast to the living body tissue, control intrusion and development of an osteoclast and a collagen fiber promoting hardening of the soft tissue, and also control hardening of the bone tissue and not to inhibit intrusion of erythrocytes and body fluid and development of capillary blood vessels.

In order to satisfy these requirements, it is important that a filler or prosthetic material to be inserted into a living body have good compatibility with the living body, especially good bioresponsibility, should provide a residence propagation space suitable for the activation of desired cells, and should prevent intrusion of undesirable cells and hardening of the bone tissue by abnormal development of a collagen fiber.

SUMMARY OF THE INVENTION

It is a primary object of the present invention to provide a porous ceramic material suitable for regeneration of the bone tissue in a living body, that is, induction of a new-born bone or other medical purposes or valuable as an electronic material or a genetic engineering material, processes for the preparation therof, and a method of remedying a defect of bone of a human or animal.

Other objects and advantages of the present invention will be apparent from the following description.

In one aspect of the present invention, there is provided a porous ceramic material comprising a sintered porous body of a calcium phosphate compound, wherein a multiplicity of capillary void paths having a diameter of 1 to 30 $\mu$m and a multiplicity of pores having a size of 1 to 600 $\mu$m are formed in the sintered porous body and at least part of the pores are connected to the exterior space of the sintered porous body through at least a part of the capillary void paths. The multiplicity of pores may be connected to one another through a part of the capillary void paths.

In another aspect of the present invention, there are provided processes for the preparation of the above-mentioned porous ceramic material.

One process of the preparation of the porous ceramic material of the present invention comprises bubbling 100 parts by weight of albumen to form a multiplicity of bubbles having a diameter of 1 to 600 $\mu$m, incorporating the bubbled albumen with 30 to 120 parts by weight of a calcium phosphate compound powder, shaping the thus-obtained mixture by casting the mixture into a mold havig a desired size and shape, heating the shaped mixture at a temperature of 120° to 150° C. to harden the albumen, then heating the shaped mixture at a temperature of 500° to 700° C. to carbonize the hardened albumen, and then heating the shaped mixture at a temperature of 800° to 1,350° C. in an oxygen-containing atmosphere to remove the carbonization product by burning and sinter the calcium phosphate compound powder.

Another process for the preparation of the porous ceramic material of the present invention comprises bubbling 100 parts by weight of albumen to form a multiplicity of bubbles having a diameter of 1 to 600 $\mu$m, incorporating the foamed albumen with 30 to 120 parts by weight of a calcium phosphate compound powder and 1 to 5 parts by weight of an organic fiber having a length of 5 μm to 5 mm and a diameter of 1 to 30 μm, shaping the thus-obtained mixture by casting the mixture into a mold having a desired shape and size, heating the shaped mixture at a temperature of 120° to 150° C. to harden the albumen, heating the shaped mixture at a temperature of 500° to 700° C. to carbonize the hardened albumen and organic fiber, and then heating the shaped mixture at a temperature of 800° to 1,350° C. in an oxygen-containing atmosphere to remove the carbonization product by burning and sinter the calcium phosphate compound powder.

Still another process for the preparation of the porous ceramic material of the present invention comprises mixing 20 to 300 parts by weight of a sublimable solid substance powder having a particle size of 1 to 600 μm with 100 parts by weight of a calcium phosphate compound powder, press-shaping the thus-obtained mixture into a desired shape and size, heating the shaped mixture at a temperature of 300° to 500° C. to remove the sublimable substance by sublimation, and then heating the residual shaped product at a temperature of 800° to 1,350° C. to sinter the calcium phosphate compound powder.

Still another process for the preparation of the porous ceramic material of the present invention comprises incorporating 20 to 300 parts by weight of a sublimable solid substance powder having a particle size of 1 to 600 μm and 1 to 5 parts by weight of an organic fiber having a length of 5 μm to 5 mm and a diameter of 1 to 30 μm with 100 parts by weight of a calcium phosphate compound powder, press-shaping the thus-obtained mixture to a desired shape and size, heating the shaped mixture at a temperature of 200° to 800° C. to remove the sublimable substance by sublimation and carbonize the organic fiber, and then heating the shaped mixture at a temperature of 800° to 1,350° C. in an oxygen-containing atmosphere to remove the carbonization product by burning and sinter the clacium phosphate compound powder.

Still another process for the preparation of the porous ceramic material of the present invention comprises mixing 25 to 380 parts by weight of organic synthetic resin particles having a particle size of 1 to 600 μm with 100 parts by weight of a calcium phosphate compound powder, press-shaping the thus-obtained mixture into a desired shape and size, heating the shaped mixture at a temperature of 200° to 800° C. to remove the organic synthetic resin particles by thermal decomposition, and heating the residual shaped product at a temperature of 800° to 1,350° C. in an oxygen-containing atmosphere to sinter the calcium phosphate compound powder.

Still another process for the preparation of the porous ceramic material of the present invention comprises incorporating 25 to 380 parts by weight of organic synthetic resin particles having a particle size of 1 to 600 μm and 1 to 5 parts by weight of an organic fiber having a length of 5 μm to 5 mm and a diameter of 1 to 30 μm with 100 parts by weight of a calcium phosphate compound powder, press-shaping the thus-obtained mixture into a desired shape and size, heating the shaped mixture at a temperature of 200° to 800° C. to remove the organic synthetic resin by thermal decomposition and carbonize the organic fiber, and then heating the shaped mixture at a temperature of 800° to 1,350° C. in an oxygen-containing atmosphere to remove the carbonization product by burning and sinter the calcium phosphate compound powder.

Still another process for the preparation of the porous ceramic material of the present invention comprises incorporating 25 to 380 parts by weight of organic synthetic resin particles having a particle size of 1 to 600 μm and 2 to 5 parts by weight of sublimable solid substance particles having a particle size of 1 to 600 μm with 100 parts by weight of a calcium phosphate compound powder, press-shaping the thus-obtained mixture into a desired shape and size, heating the shaped mixture at a temperature of 200° to 800° C. to remove the organic synthetic resin particles by thermal decomposition and remove the sublimable substance particles by sublimation, and then heating the residual shaped product at a temperature of 800° to 1,350° C. in an oxygencontaining atmosphere to sinter the calcium phosphate compound powder.

Still another process for the preparation of the porous ceramic material of the present invention comprises incorporating 25 to 380 parts by weight of organic synthetic resin particles having a particle diameter of 1 to 600 μm, 2 to 5 parts by weight of sublimable solid substance particles having a particles size of 1 to 600 μm and 1 to 5 parts by weight of an organic fiber having a length of 1 to 5 mm and a diameter of 5 μm to 30 μm with 100 parts by weight of a calcium phosphate compound powder, press-shaping the thus-obtained mixture into a desired shape and size, heating the shaped mixture at a temperature of 200° to 800° C. to remove the organic synthetic resin particles by thermal decomposition, remove the sublimable substance particles by sublimation and carbonize the organic fiber, and then heating the shaped mixture at a temperature of 800° to 1,350° C. in an oxygen-containing atmosphere to remove the carbonization product by burning and sinter the calcium phosphate compound powder.

In still another aspect of the present invention, there is provided a method for inducing a new-born bone which comprises filling or embedding the above-mentioned porous ceramic material in a defect of bone of human or animal whereby a new-born bone is induced while intrusion of collagen fibers and osteoclasts into the porous ceramic material is restricted.

DESCRIPTION OF THE PREFERRED EMBODIMENTS

The porous ceramic material of the present invention is composed of a sintered porous body of a calcium phosphate compound. The calcium phosphate compound used in the present invention comprises as main ingredients $CaHPO_4$, $Ca_3(PO_4)_2$, $Ca_5(PO_4)_3OH$, $Ca_4O(PO_4)_2$, $Ca_{10}(PO_4)_6(OH)_2$, $CaP_4O_{11}$, $Ca(PO_3)_2$, $Ca_2P_2O_7$, and $Ca(H_2PO_4)_2 \cdot H_2O$ and includes a series of compounds called "hydroxyapatite". Hydroxyapatite comprises as a basic component a compound having a composition formula $Ca_5(PO_4)_3OH$ or $Ca_{10}(PO_4)_6(OH)_2$. A part of the Ca component may be substituted by one or more members selected from Sr, Ba, Mg, Fe, Al, Y, La, Na, K and H and a part of the ($PO_4$) component may be substituted by one or more members selected from $VO_4$, $BO_3$, $SO_4$, $CO_3$ and $SiO_4$. Moreover, a part of the (OH) component may be substituted by one or more members selected from F, Cl, O and $CO_3$. The hydroxyapatite may be an ordinary crystal, or it may be an isomorphorous solid solution, a substitutional solid solution or an interstitial solid solution. Moreover, the hydroxyapatite may contain non-stoichiometric lattice defects.

It is ordinarily preferred that the atomic ratio of calcium (Ca) to phosphorus (P) in the calcium phosphate compound used in the present invention be in the range of from 1.30 to 1.80, especially from 1.60 to 1.67.

As the calcium phosphate compound used in the present invention, tricalcium phosphate [$Ca_3(PO_4)_2$], hydroxyapatite [$Ca_5(PO_4)_3OH$], and hydroxyapatite [$Ca_{10}(PO_4)_6(OH)_2$] are preferred. Those which are synthesized according to the sol-gel method and then freeze-dried are especially preferred. It is preferred that the calcium phosphate compound be one sintered at 800° to 1,350° C., more preferably at 850° to 1,200° C..

In the porous ceramic material of the present invention, the calcium phosphate porous body may have any shape and size. In the interior of the porous body, there are formed a multiplicity of capillary void paths extending in a slender elongated form and a multiplicity of pores having a diameter of 1 to 600 μm, especially 3 to 300 μm. The diameter of the capillary void paths is 1 to 30 microns, preferably 1 to 20 microns. The pores are connected to the exterior space of the porous body through at least a part of the multiplicity of capillary void paths. Ordinarily, the multiplicity of pores are connected to one another through a part of the capillary void paths.

It is preferred that the sintered porous body have a porosity of 40 to 90%, more preferably 60 to 70%.

It is preferred that the pores in the sintered porous body should have a shape of a true sphere or a similar shape. It also is preferred that the pores be uniformly distributed in the porous body. These pores provide residence spaces for biophysically activating osteolytic cells and osteoblasts when the ceramic material is embedded in a living body. Osteoblasts and the like tend to stay in these pores, especially spherical pores. Accordingly, it is indispensable that the pores have a diameter of 1 to 600 μm, preferably 3 to 300 μm. Pores having a size outside the range of from 1 to 600 μm fail to provide good residence spaces for the above-mentioned cells.

If the pores have a shape of a true sphere or a similar shape, the mechanical strengths of the obtained porous material are high. Accordingly, when this porous material is embedded in a living body, it continues to hold these high mechanical strengths until it is turned over to a new-born bone. Thus, fracture of a bone is prevented during this period.

The capillary void paths in the sintered porous body connect the pores at least to the exterior space of the porous body. Osteolytic cells, osteoblasts, erythrocytes and body fluid are allowed to freely penetrate into the porous body through these capillary voids, whereby development of capillary blood vessels is promoted. However, since the diameter of the capillary void paths is 1 to 30 μm, preferably 1 to 20 μm, almost no osteoclasts and collagen fibers are allowed to penetrate into the capillary void paths within the porous body, whereby abnormal growth of collagen fibers and hardening of the bone tissue can be prevented. Namely, in the porous body of the present invention, the capillary void paths exert a function of a biofilter.

If the diameter of the capillary void paths is smaller than 1 μm, intrusion of osteolytic cells, osteoblasts, erythrocytes and body fluid into the porous body becomes difficult. If the diameter of the capillary void paths is larger than 30 μm, intrusion and growth of osteoclasts and collagen fibers are allowed and therefore, regeneration of the bone is inhibited, resulting in hardening of the neighboring tissue.

In the porous ceramic material of the present invention, the pores in the porous body may be connected to one another by a part of the multiplicity of capillary voids paths, whereby consumption of the porous body and regeneration (turnover) of the living body tissue are promoted and resorption of bone with age can be controlled.

The porous ceramic material of the present invention can freely be processed easily to a shape and size corresponding to a shape and size of a defect or antrum to be filled or embedded. The ceramic material of the present invention may be shaped into granules having a size of 0.05 to 5 mm.

When the porous ceramic material of the present invention is embedded as a filler or prosthetic material, blood, body fluid, osteolytic cells and osteoblasts penetrate into the porous body through the capillary void paths, and the porous body is eaten and consumed by osteolytic cells propagated in the pores. Simultaneously, the bone tissue is regenerated by the osteoblasts and so-called turnover is performed. Since the capillary void paths connecting the pores to the exterior space of the porous body have a diameter of 1 to 30 μm, almost no osteoclasts or collagen fibers are allowed to penetrate into the capillary void paths within the porous body, and therefore, abnormal growth and hardening of the collagen fibers can be prevented. Accordingly, the soft tissue of the regenerated bone is neither destroyed nor hardened by the collagen fibers. Therefore, the porous ceramic material of the present invention induces new-born bone and is substituted by normal bone tissue growing in a living body.

A porous ceramic material that can be turned over to normal bone tissue in the above-mentioned manner is novel. This porous ceramic material has been realized for the first time according to the present invention.

The porous ceramic material of the present invention can be prepared according to various processes.

A first process for the preparation of the porous ceramic material comprises bubbling 100 parts by weight of albumen to form a multiplicity of bubbles having a diameter of 1 to 600 μm, mixing the bubbled albumen with 30 to 120 parts by weight of a calcium phosphate compound powder, shaping the thus-obtained mixture by casting the mixture into a mold having a desired shape and size, heating the shaped mixture at a temperature of 120° to 50° C. to harden the albumen, heating the shaped mixture at a temperature of 500° to 700° C. to carbonize the albumen, and then heating the shaped mixture at a temperature of 800° to 1,350° C. in an oxygen-containing (and, if necessary, moisture-containing) atmosphere to remove the carbonization product by burning and sinter the calcium phosphate compound powder.

It is generally preferred that the particle size of the calcium phosphate compound powder used for the preparation of the porous ceramic material of the present invention be 0.05 to 10 μm. It is especially preferred that the calcium phosphate compound powder contain a crystalline portion grown in the form of a plate and have a particle size distribution, determined by a scanning electron microscope (SEM) such that no more than 30% of the particles of the powder have a particle size of at least 1 μm and at least 70% of the particles of the powder have a particle size of smaller than 1 μm.

An optional method may be adopted for forming bubbles having a desired size in albumen. For example, albumen is whipped by an emulsifying mixer, a sample of the bubbled albumen is collected on a slide glass by passing the slide glass on the liquid surface of the bubbled albumen and measuring the size of foams by a microscope. This operation is repeated until the desired size is obtained. Then, a predetermined amount of the calcium phosphate compound powder is incorporated with the foamed albumen and stirring is conducted. At this step, a small amount of a bubble regulating agent, for example, a fatty acid such as oleic acid or maleic acid and/or an aliphatic alcohol such as isopropyl alcohol or isobutyl alcohol may be added.

The thus-obtained mixture is formed into a predetermined shape and size. Shaping methods and apparatuses customarily used for the production of sintered products may optionally be used. Ordinarily, however, a casting method using a mold is adopted.

The shaped mixture is heated at a temperature of 120° to 150° C., preferably for 60 to 120 minutes, to harden the albumen. It is preferred that the relative humidity of the heating atmosphere be adjusted to 30 to 70%, and it also is preferred that the temperature elevating rate be controlled to 5° to 10° C./min. The hardened albumen reinforces the framework of bubbles.

Then, the shaped mixture is heated at a temperature of 500° to 700° C., preferably for 120 to 180 minutes, to carbonize the hardened albumen. Then, the shaped mixture is heated at a temperature of 800° to 1,350° C., preferably 850° to 1,200° C. in an oxygen-containing atmosphere, for example, air, to remove the carbonization product by burning and sinter the calcium phosphate compound powder. The oxygen-containing atmosphere may contain moisture, if desired. At this step, the heating time is ordinarily about 1 to about 3 hours.

Gases generated by coagulation and carbonization of albumen and combustion of the carbonization product escape from the interior of the porous body to the outside. At this time, many capillary void paths are formed and pores corresponding to the bubbles in the whipped albumen are formed. The pores are connected to the exterior space of the porous body through the capillary void paths, and ordinarily, the pores are connected to one another through the capillary void paths.

In the above-mentioned preparation process, 1 to 5 parts by weight of an organic fiber having a length of 5 μm to 5 mm and a diameter of 1 to 30 μm can be added together with the bubbled albumen to 100 parts of the calcium phosphate compound powder. In this case, after the albumen-hardening heating step, the shaped mixture is heated at a temperature of 500° to 700° C., preferably for 120 to 180 minutes, to carbonize the albumen and the organic fiber. The resulting carbonization product is removed by burning at the subsequent sintering heating step.

In this process, the organic fiber has an effect of ensuring formation of capillary void paths substantially having a uniform diameter of 1 to 30 μm. The kind of organic fiber used is not particularly restricted, so far as it has a a diameter of 1 to 30 μm and it can be completely burnt. However, a fiber of an animal such as cat, raccoon, dog or mouse, especially a belly hair fiber, a natural organic fiber such as a silk fiber or a cellulose fiber, or an organic synthetic fiber such as a polyester, polypropylene, polyamide or polyacrylic fiber is preferably used.

Another process for the preparation of the porous ceramic material of the present invention comprises incorporating 20 to 300 parts by weight of sublimable solid substance particles having a particle size of 1 to 600 μm with 100 parts by weight of a calcium phosphate compound powder, press-shaping the thus-obtained mixture into a desired shape and size, heating the shaped mixture at a temperature of 200° to 800° C. to remove the sublimable substance by sublimation, and heating the residual shaped product at a temperature of 800° to 1,350° C. to sinter the calcium phosphate compound powder.

The same calcium phosphate compound powder as used in the above-mentioned process is used in this process. The sublimable solid substance powder is added to form pores having a predetermined diameter of 1 to 600 μm in the porous body. The kind of the sublimable substance is not particularly restricted, so far as it is easily sublimated at a temperature of 200° to 800° C. without any substantial residue being left. At least one member selected from camphor, menthol and naphthalene is ordinarily used as the sublimable substance.

The mixture of the sublimable substance powder and the calcium phosphate compound powder is press-shaped into a desired shape and size. The press-shaping method is not particularly restricted. Ordinary static pressure press-shaping methods such as a rubber press method and a CIP method may be adopted. The resulting shaped mixture is heated at a temperature of 200° to 800° C., preferably for 120 to 180 minutes, whereby capillary void paths connecting pores to the exterior space of the porous body and to one another are formed by sublimation and escape of the fine powder of the sublimable substance.

Then, the residual shaped product is heated at 800° to 1,350° C., preferably 850° to 1,200° C. for 1 to 3 hours, to sinter the calcium phosphate compound powder.

In this process, by adjusting the shape and particle size of the sublimable substance powder, the shape and size of the pores can be controlled more easily than in the process using albumen.

In the above-mentioned process using the sublimable substance powder, 1 to 5 parts by weight of an organic fiber having a length of 5 μm to 5 mm and a diameter of 1 to 30 μm may be further added to 100 parts by weight of the calcium phosphate compound powder. If the resulting mixture is heated at a temperature of 200° to 800° C., preferably for 120 to 180 minutes, the sublimable substance is sublimated and removed and the organic fiber mixture is carbonized. Then, the mixture is heated at a temperature of 800° to 1,350° C., preferably for 1 to 3 hours, in an oxygen-containing (and, if necessary, moisture-containing) atmosphere, whereby the carbonization product is burnt away and the calcium phosphate compound powder is sintered.

In this process, the incorporated organic fiber is effective for ensuring formation of substantially uniform capillary void paths having a diameter of 1 to 30 μm. The same organic fibers as described above can be used.

If a volatile lower alcohol such as methanol or ethanol is added at the step of incorporating the organic fiber or sublimable substance powder into the calcium phosphate compound powder, a homogeneous mixture can easily be obtained, the particle size of the sublimable substance powder can be controlled and the adhesion between the sublimable substance powder and the organic fiber can be improved, whereby formation of capillary void paths communicating with the pores can be promoted.

Still another process for the preparation of the porous ceramic material of the present invention comprises incorporating 25 to 380 parts by weight of organic synthetic resin particles having a particle size of 1 to 600 μm with 100 parts by weight of a calcium phosphate compound powder, press-shaping the thus-obtained mixture into a desired shape and size, heating the shaped mixture at a temperature of 200° to 800° C. to remove the organic synthetic resin particles by thermal decomposition, and then heating the residual shaped product at a temperature of 800° to 1,350° C. to sinter the calcium phosphate compound powder.

The organic synthetic resin particles having a particle size of 1 to 600 μm, which are used in the above process, are effective for forming pores having a diameter of 1 to 600 μm in the porous body. The kind of organic synthetic resin is not particularly restricted, so far as the resin is thermally decomposed at a temperature of 200° to 800° C. and removed from the porous body. Ordinarily, a thermoplastic synthetic resin such as polymethyl methacrylate, polypropylene or polystyrene is used. Of these, polymethyl methacrylate is most preferred. Since the organic synthetic resin has an appropriate rigidity, when particles of the organic synthetic resin is mixed with the calcium phosphate compound powder or the resulting mixture is press-shaped, the spherical particles are neither deformed nor crumbled and therefore, pores having a shape and size agreeing precisely with the shape and size of the organic synthetic resin particles can be formed.

The mixture of the organic synthetic resin spherical particles and the calcium phosphate compound powder is press-shaped into a desired shape and size. The shaping method is not particularly restricted, and an ordinary static pressure press-shaping method such as a rubber press method or a CIP method may be adopted. The resulting shaped mixture is heated at a temperature of 200° to 500° C., preferably at a temperature of 300° to 350° C. for 120 to 180 minutes, to remove the organic synthetic resin particles by thermal decomposition, thereby corresponding pores and capillary void paths extending from these pores are formed.

Then, the shaped product is heated at a temperature of 800° to 1,350° C., preferably at a temperature of 850° to 1,200° C. for 1 to 30 hours, in an oxygen-containing (and, if necessary, moisture-containing) atmosphere to sinter the calcium phosphate compound powder. Even if there is a thermal decomposition residue of the organic synthetic resin particles present, this residue is burnt and removed at the sintering heating step.

In the process using the organic synthetic resin particles, 1 to 5 parts by weight of an organic fiber having a length of 5 μm to 5 mm and a diameter of 1 to 30 μm may be further added to 100 parts by weight of the calcium phosphate compound powder. The kind and effect of the organic fiber are the same as described above.

In the above-mentioned process using organic synthetic resin particles, 2 to 5 parts by weight of sublimable solid substance particles having a particle size of 1 to 600 μm may be further added to 100 parts by weight of the calcium phosphate compound powder. The kind of the sublimable substance is the same as described above. In this process, the sublimable substance particles have a particle size of 1 to 600 μm and are effective for formation of capillary void paths.

Moreover, in the above-mentioned process using organic synthetic resin particles, 2 to 5 parts by weight of an organic fiber having a length of 5 μm to 5 mm and a diameter of 1 to 30 μm and 2 to 5 parts by weight of sublimable solid substance particles having a particle size of 1 to 600 μm may be further added to 100 parts by weight of the calcium phosphate compound powder. The kinds and effects of the organic fiber and sublimable solid substance particles are the same as described above.

The porous ceramic material of the present invention has pores having a diameter of 1 to 600 μm, preferably 3 to 300 μm, and capillary void paths having a diameter of 1 to 30 μm, preferably 1 to 20 μm. Since the capillary void paths function as a biofilter, they control intrusion and abnormal development of collagen fibers, hardening of the bone tissue by the catalytic action of collagen fibers and intrusion of osteoclasts inhibiting induction of new-born bone. Furthermore, hardening of collagen fibers by abnormal development thereof is prevented and only osteolytic cells, osteoblasts, erythrocytes and body fluid are selectively allowed to permeate. Moreover, the pores having a specific pore size promote the activation of osteolytic cells and osteoblasts at a cell level. Accordingly, when the porous ceramic material of the present invention is used, it is possible to promote induction of a new-born bone and turnover of a bone while keeping a good compatibility with a living body.

In the porous ceramic material of the present invention, at least part of the pores must be connected to the exterior space through the capillary void paths and at least part of the pores are connected to one another through the capillary void paths. It is preferable that all of the pores are connected to the exterior space and to one another through the capillary void paths. In addition, the capillary void paths in the porous ceramic body of the present invention are very fine paths having a diameter to 1 to 30 μm, preferably 1 to 20 μm. Accordingly, induction of new-born bone can be accomplished very effectively. More specifically, when the porous ceramic material is embedded in a certain bone, since the diameter of the capillary voids is as small as 1 to 30 μm, preferably 1 to 20 μm, almost no intrusion of collagen fibers into the capillary void paths is allowed and hardening of collagen fibers can be prevented. Only osteolytic cells, osteoblasts, erythrocytes and body fluid effective for induction of a new-born bone are selectively allowed to penetrate through the capillary void paths with the result that a very soft bone is first formed. This structure gradually develops to the outside to effect organization of the bone, whereby a structure comprising the marrow in the central portion and a hardened tissue in the pheripheral portion, as in case of a natural bone of a human or animal, is formed. In case of the conventional apatite porous body, however, since the size and shape of pores cannot be controlled and the pores allow intrusion of collagen fibers, even if new-born bone is induced, the embedded porous body is hardened by the catalytic action and abnormal development of collagen fibers, and there is a risk of inflammation from a part near the embedded portion or generation of a cancer. In case of the porous ceramic body of the present invention, for the reasons set forth above, a structure quite similar to that of a natural bone of a human or animal, which comprises marrow in the central portion and a tissue having an increased bone density in the peripheral portion, can be produced. This structure is different from a structure composed solely of a hardened bone, which is formed by the conventional apatite porous body, and tough new-born bone having the same structure as that of natural bone can be produced. Namely, when the porous ceramic material is embedded in existing bone, the porous body of the present invention is eaten away and consumed. Instead, new-born bone having the same structure as that of natural bone is induced and tough and flexible bone which is non-toxic for a long time is formed. As pointed out hereinbefore, if the porous ceramic body of the present invention having the above-mentioned specific structure is used, a soft bone corresponding to the marrow is first formed as in case of a natural bone. This marrow is organized toward the inside and the bone density is increased toward the outside, with a result that soft and flexible bone quite similar to natural bone of human or animals is formed.

The porous ceramic material of the present invention having capillary void paths and pores can be used not only as a biological material as described above but also as an electronic material for integrated circuits (IC) or large-scale integrated circuits (LSI) and an intermediate material for genetic engineering.

When the porous ceramic material is filled or embedded in a defect of bone of human on animals, it functions as a biofilter, namely, osteolylic cells, osteoblasts, erythrocytes and body fluid are selectively allowed to intrude through the porous ceramic material while almost no intrusion of osteoclasts and collagen fibers is allowed. Thus, new-born bone having the same structure as that of natural bone of human or animals is formed. Accordingly, the porous ceramic material can be utilized for inducing new-born, or, controlling resorption of bone with age, and thus, is useful for remedying bone defects.

The present invention will be further described by the following examples.

EXAMPLE 1

A mixture of 100 g albumen and 3 g of oleic acid was whipped by an emulsifying mixer. A slide glass was sometimes passed on the liquid surface to effect sampling. The sample was observed by a microscope. Whipping was continued in this manner until the minimum size of bubbles of the albumen was 3 $\mu$m. To the bubbled albumen was added 90 g of synthetic hydroxyapatite [$Ca_5(PO_4)_3OH$, Ca/P atomic ratio=1.67, particle size=0.05 to 10 $\mu$m]. The mixture was shaped by casting it into a mold. The shaped mixture was heated to 150° C. at a temperature elevating rate of 10° C./min in an atmosphere having a relative humidity of 30%. The shaped mixture was maintained at this temperature for 180 minutes to harden the albumen and construct a framework of the bubbles. Then, the shaped mixture was heated at 500° C. for 120 minutes to carbonize the hardened albumen. Finally, the shaped mixture was heated at 1,000° C. in air for 60 minutes to sinter the hydroxyapatite powder.

The obtained porous body has a porosity of 76%. When the porous body was examined by a microscope, it was found that there were present many pores having a diameter of 10 to 500 $\mu$m and many capillary void paths having a diameter of 12 $\mu$m. The pores were connected to the exterior space and to one another through the capillary void paths.

A cubic sample having a size of 1 cm×1 cm×1 cm was cut out from the porous body and the uniaxial compression strength was measured. It was found that the uniaxial compression strength was 12 kg/cm$^2$.

EXAMPLE 2

The procedures of Example 1 were repeated except that 5 g of a polypropylene fiber (length=5 to 10 $\mu$m diameter=3 to 10 $\mu$m) was further added at the albumen whipping step. The obtained porous body had pores and capillary void paths similar to those of the porous body obtained in Example 1, and many capillary void paths having a diameter of 5 to 10 $\mu$m were observed.

The uniaxial compression strength of the porous body was 10 kg/cm$^2$.

EXAMPLE 3

Commercially available camphor according to the Japanese Pharmacopeia was pulverized and particles having a particle size of 1 to 600 $\mu$m were collected by sieving. Then, 40 g of powdery hydroxyapatite (the same as described in Example 1) was homogeneously mixed with the camphor particles. The mixture was pressed under a static pressure of 2 kg/cm$^2$ by a rubber press-shaping machine and allowed to stand for about 10 minutes. The shaped mixture was heated at 350° C. for 180 minutes and then heated at 1,000° C. for 60 minutes in air.

The obtained porous shaped article had a porosity of 77% and a uniaxial compression strength of 30 kg/cm$^2$. The porous body had many pores having a diameter of 100 to 500 $\mu$m (300 $\mu$m on the average) and many capillary void paths having a diameter of 1 to 30 $\mu$m.

EXAMPLE 4

The procedures of Example 3 were repeated except that 5 g of the same polypropylene fiber as described in Example 2 was further added. After heating at 350° C., the shaped mixture was further heated at 500° C. for 120 minutes to carbonize the fiber.

Among capillary void paths formed in the obtained porous body, there were observed many capillary void paths having a diameter of about 5 to about 10 $\mu$m.

The obtained porous body has a porosity of 68% and a uniaxial compression strength of 28 kg/cm$^2$.

EXAMPLE 5

60 g of polymethyl methacrylate particles having a shape of a true sphere (particle size=30 to 300 $\mu$m, average particle size of about 100 $\mu$m), 50 g of hydroxyapatite particles (the same as described in Example 1) and a small amount of methyl alcohol were homogeneously mixed under heating.

Just before sufficient drying, the mixture was pressed under a static pressure of 2 kg/cm$^2$ for about 10 minutes by a rubber press-shaping machine. The shaped mixture was heated at 350° C. for 180 minutes to thermally decompose the polymethyl methacrylate particles, and then the shaped product was heated at 1,000° C. in air for 1 hour.

The obtained sintered porous body had a porosity of 70% and a uniaxial compression strength of 80 kg/cm$^2$. The porous body had many pores of a truly spherical shape having a diameter of 30 to 300 $\mu$m and many capillary void paths having a diameter of 2 to 10 $\mu$m.

EXAMPLE 6

The procedures of Example 5 were repeated except that 2 g of a disinfected and degreased belly hair of a cat (frozen cat belly hair cut by a crystat and dried; diameter=2 to 10 $\mu$m length=about 5 to about 10 mm) was further added to the mixture of the polymethyl methacrylate particles and hydroxyapatite powder. After heating at 350° C., the shaped mixture was heated at 750° C. for 120 minutes to carbonize the cat hair.

The obtained porous body had a porosity of 73% and a uniaxial compression strength of 90 kg/cm$^2$. Spherical pores and capillary void paths similar to those of the porous body of Example 5 were observed. Furthermore, formation of many capillary void paths having a diameter of 2 to 10 μm was confirmed.

EXAMPLE 7

The procedures of Example 5 were repeated except that 3 g of camphor powder having a particle size of 1 to 600 μm was further added to the mixture of the polymethyl methacrylate particles and hydroxyapatite powder, the mixture was press-shaped by a rubber press-shaping machine before complete drying and after heating at 350° C., and the shaped mixture was further heated at 500° C. for 120 minutes to remove camphor by sublimation.

The obtained sintered porous body had a porosity of 65% and a uniaxial compression strength of 160 kg/cm$^2$.

The porous body had spherical pores and capillary void paths similar to those of the porous body obtained in Example 5.

EXAMPLE 8

The procedures of Example 5 were repeated except that 2 g of the same cat hair as described in Example 6 and 3 g of the same camphor powder as described in Example 7 were further added to the mixture of the polymethyl methacrylate particles and hydroxyapatite powder, methyl alcohol was kneaded with the mixture, the mixture was shaped by a rubber press-shaping machine. After heating at 350° C., the shaped mixture was further heated at 750° C. for 120 minutes to carbonize the cat hair and remove camphor by sublimation.

The obtained sintered porous body had a porosity of 76% and a high compression strength of 110 kg/cm$^2$.

In the porous body, spherical pores and capillary void paths similar to those of the porous body of Example 5 were formed, and it was found that among these void paths, many capillary void paths having a diameter of 2 to 10 μm were presented.

EXAMPLE 9

Columns having a diameter of 0.5 cm and a length of 1 cm were cut out from the porous bodies obtained in Examples 1 through 8. They were filled in defects formed by surgical treatment on thigh bones of beagle dogs. After 2 weeks passed from the embedment, incision and observation were performed. In each case, prominent induction of a new-born bone was observed in the spherical pores. After a lapse of 2 to 3 months, development of new-born bone from the peripheral portion of the porous body to the interior thereof was observed. It was confirmed that so-called turnover was favorably advanced without abnormal growth of collagen fibers or hardening of the tissue.

EXAMPLE 10

60 g of polymethyl methacrylate particles of a shape of a true sphere (particle size 32 30−300 μm, average particle size=about 100 μm), 50 g of hydroxyapatite particles [Ca$_5$(PO$_4$)OH, Ca/P atomic ratio=1.67, particle size=0.05-10 μm], 3 g of a camphor powder having a particle size of 300 μm, a fiber obtained by cutting a disinfected, degreased and frozen belly hair of a cat, which had a diameter of 2 to 10 μm and a length of 5 to 10 μm, and a small amount of methyl alcohol were homogeneously mixed together under heating. Before sufficient drying, the mixture was shaped under a static pressure of 2 kg/cm$^2$ for 10 minutes by using a rubber press. The shaped mixture was heated at 350° C. for 180 minutes to thermally decompose the polymethyl methacrylate particles and then heated at 1,000° C. for 1 hour.

The obtained sintered porous body had a porosity of 73% and a uniaxial compression strength of 110 kg/cm$^2$. It included therein many truly spherical pores having a diameter of 30 to 300 μm and many capillary void paths having a diameter of 2 to 10 μm.

Columns having a diameter of 0.5 cm and a length of 1 cm were cut out from the so-obtained porous body. They were filled in defects formed by surgical treatment on a thigh bone of a beagle dog. After 2 weeks passed from the embedment, incision and observation were performed. Prominent induction of new-born bone was observed in the truly spherical pores. After a lapse of 2 to 3 months, development of new-born bone from the peripheral portion of the porous body to the interior space thereof was observed. It was confirmed that so-called turnover was favorably advanced without abnormal growth of collagen fibers or hardening of the tissue.

From the results of optical microscope observation, it was confirmed that osteolytic cells and osteoblasts selectively intruded and they were present in the pores of the porous body according to the method of the present invention.

We claim:

1. A process for the preparation of a porous ceramic material, which comprises the steps of:
   bubbling 100 parts by weight of albument to form a multiplicity of bubbles having a size of 1 to 600 μm;
   incorporating the bubbled albumen with 30 to 120 parts by weight of a calcium phosphate compound powder and 1 to 5 parts by weight of an organic fiber having a length of 5 μm to 5 mm and a diameter of 1 to 30 μm,
   shaping the thus-obtained mixture into a desired shape and size,
   heating the shaped mixture at a temperature of 120° to 150° C. to harden the albumen;
   heating the hardened shaped mixture at a temperature of 500° to 700° C. to carbonize the hardened albumen and organic fiber; and then,
   heating the carbonized shaped mixture at a temperature of 800° to 2,350° C. in an oxygen-containing atmosphere to remove the carbonization product by burning and to sinter the calcium phosphate compound powder.

2. A process according to claim 1, wherein the step of heating the shaped mixture for the hardening of albumen is carried out in an atmosphere having a relative humidity of 30 to 70% at a temperature-elevating rate of 5° to 10° C./min.

3. A process according in claim 1, wherein the calcium phosphate compound powder has a particle diameter 0.05 to 10 μm.

4. A process according to claim 1, wherein the organic fiber is at least one member selected from an animal fiber, a silk fiber, a cellulose fiber and an organic synthetic fiber.

5. A process for the preparation of a porous ceramic material, which comprises the steps of:
   mixing 20 to 300 parts by weight of sublimable solid substance particles having a particle diameter of 1 to 600 μm and 1 to 5 parts by weight of an organic fiber having a length of 5 μm to 5 mm and a diameter of 1 to 30 μm with 100 parts by weight of a calcium phosphate compound powder;

press-shaping the thus-obtained mixture into a desired shape and size;

heating the shaped mixture at a temperature of 200° to 800° C. to remove the sublimable substance by sublimation and carbonize the organic fiber; and then, heating the shaped mixture at a temperature of 800° to 1,350° C. in an oxygen-containing atmosphere to remove the carbonization product by burning and sinter the calcium phosphate compound powder.

6. A process according to claim 5, wherein the calcium phosphate compound powder has a particle diameter of 0.05 to 10 μm.

7. A process according to claim 5, wherein the sublimable solid substance is at least one member selected from the group consisting of camphor, menthol and naphthalene.

8. A process according to claim 5, wherein the organic fiber is at least one member selected from the group consisting of an animal fiber, a silk fiber, a cellulose fiber and an organic synthetic fiber.

9. A process for the preparation of a porous ceramic material, which comprises the steps of:

mixing 25 to 380 parts by weight of organic synthetic resin particles having a particle diameter of 1 to 600 μm and 1 to 5 parts by weight of an organic fiber having a length of 5 μm to 5 mm and a diameter of 1 to 30 μm with 100 parts by weight of a calcium phosphate compound powder;

press-shaping the thus-obtained mixture into a desired shape and size;

heating the shaped mixture at a temperature of 200° to 800° C. to remove the organic synthetic resin by thermal decomposition and carbonize the organic fiber; and then, heating the shaped mixture at a temperature of 800° to 1,350° C. in an oxygen-containing atmosphere to remove the carbonization product by burning and sinter the calcium phosphate compound powder.

10. A process according to claim 9, wherein the calcium phosphate compound powder has a particle diameter of 0.05 to 10 μm.

11. A process according to claim 9, wherein the organic synthetic resin is at least one member selected from the group consisting of polymethyl methacrylate, polypropyelne and polystyrene.

12. A process according to claim 9, wherein the organic fiber is at least one member selected from the group consisting of an animal fiber, a silk fiber, a cellulose fiber and an organic synthetic fiber.

13. A process according to claim 9, wherein the organic synthetic resin particles have a particle diameter of 10 to 300 μm.

14. A process for the preparation of a porous ceramic material, which comprises the steps of:

mixing 25 to 380 parts by weight of organic synthetic resin particles having a particle diameter of 1 to 600 μm, 2 to 5 parts by weight of sublimable solid substance particles having a particle diameter of 1 to 600 μm and 1 to 5 parts by weight of an organic fiber having a length of 5 μm to 5 mm and a diameter of 1 to 30 μm with 100 parts by weight of a calcium phosphate compound powder;

press-shaping the thus-obtained mixture into a desired shape and size;

heating the shaped mixture at a temperature of 200° to 800° C. to remove the organic synthetic resin particles by thermal decomposition, carbonize the organic fiber and remove the sublimable substance particles by sublimation; and then, heating the shaped mixture at a temperature of 800° to 1,350° C. in an oxygen-containing atmosphere to remove the carbonization product by burning and sinter the calcium phosphate compound powder.

15. A process according to claim 14, wherein the sublimable substance is at least one member selected from the group consisting of camphor, menthol and naphthalene.

16. A process according to claim 15, wherein the organic synthetic resin particles have a particle diameter of to 300 μm.

17. A process according to claim 14, wherein the organic synthetic particles have a particle diameter of 10 to 300 μm.

* * * * *